(12) United States Patent
Pearce

(10) Patent No.: US 6,943,198 B2
(45) Date of Patent: Sep. 13, 2005

(54) INVERT SUGAR BUBBLES

(75) Inventor: Tony M. Pearce, Alpine, UT (US)

(73) Assignee: EdiZONE, LC, Alpine, UT (US)

( * ) Notice: Subject to any disclaimer, the term of this patent is extended or adjusted under 35 U.S.C. 154(b) by 0 days.

(21) Appl. No.: 10/364,912

(22) Filed: Feb. 11, 2003

(65) Prior Publication Data

US 2003/0236339 A1 Dec. 25, 2003

Related U.S. Application Data

(60) Provisional application No. 60/356,279, filed on Feb. 11, 2002.

(51) Int. Cl.[7] ................................................ B01F 17/02
(52) U.S. Cl. ............................. 516/14; 516/18; 524/58
(58) Field of Search ............................ 524/58; 516/14, 516/18

(56) References Cited

U.S. PATENT DOCUMENTS

| | | | | |
|---|---|---|---|---|
| 3,436,459 A | * | 4/1969 | Klaui | 514/458 |
| 3,473,932 A | * | 10/1969 | Sirota et al. | 426/6 |
| 3,630,951 A | * | 12/1971 | Netherly | 516/12 |
| 3,654,166 A | * | 4/1972 | Hans-Werner et al. | 510/322 |
| 4,357,355 A | * | 11/1982 | Koch et al. | 426/4 |
| 4,514,422 A | * | 4/1985 | Yang et al. | 426/3 |
| 5,645,853 A | * | 7/1997 | Winston et al. | 424/440 |
| 6,190,705 B1 | * | 2/2001 | Richey | 426/5 |
| 6,303,164 B2 | * | 10/2001 | Cottone et al. | 426/104 |
| 6,384,089 B1 | * | 5/2002 | Tomida | 516/18 |
| 6,436,369 B2 | | 8/2002 | Barabolak et al. | 424/48 |
| 6,465,003 B2 | | 10/2002 | Ream et al. | 424/440 |
| 6,504,048 B1 | | 1/2003 | Bachmann et al. | 560/254 |
| 6,593,375 B2 | * | 7/2003 | Ammon, Jr. | 516/14 |
| 6,737,393 B2 | * | 5/2004 | Lin | 510/394 |

\* cited by examiner

*Primary Examiner*—Bernard Lipman
(74) *Attorney, Agent, or Firm*—Daniel P. McCarthy; Parsons Behle & Latimer

(57) ABSTRACT

Bubble solutions containing invert sugar are disclosed. The bubbles are long-lasting bubbles which can be produced by children at play. Components in the bubble formulation may include a water soluble polymer, invert sugar, surfactants, water, and vegetable syrup.

14 Claims, 1 Drawing Sheet

101

INVERT SUGAR BUBBLES

CROSS REFERENCE TO RELATED APPLICATIONS

PRIORITY: I hereby claim the benefit under Title 35, U.S.C. §119(e) of a U.S. Provisional Patent Application filed on Feb. 11, 2002 and having Ser. No. 60/356,279.

BACKGROUND

It has long been desired to created bubbles, blowable by children from a liquid substance, that would last a substantial amount of time before the bubbles burst and cease to exist, in conjunction with making lots of large bubbles in one blow through a standard bubble wand. The same bubbles can be used advantageously in bubble blowing toys and equipment. In the field of bubbles, there have been long lasting bubbles but these have been necessarily small and few in number from a single blow. There has also been many bubble solutions containing other types of sugars or related substances other than invert sugar. However, these other sugars or related substances do not provide the effects provided by invert sugar.

SUMMARY

Bubble solutions containing invert sugar are disclosed.

DETAILED DESCRIPTION

Figure 1:
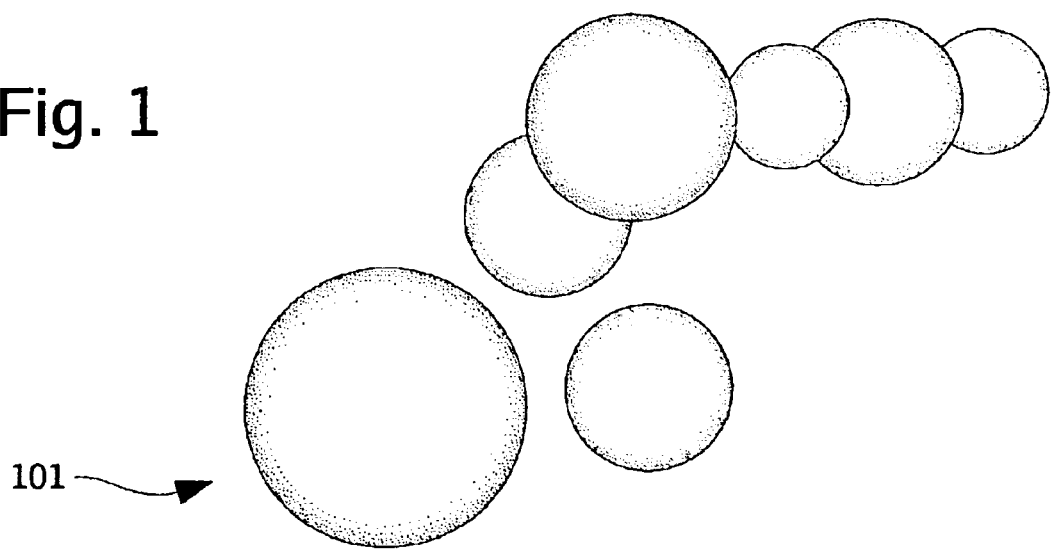
FIG. 1 depicts several large bubbles blown in a single breath from a standard bubble wand from solutions containing invert sugar, the largest being about three or more inches in diameter.

Referring to FIG. 1, several bubbles containing invert sugar 101 are depicted. These bubbles may be made from a liquid of the formulations below. Such bubbles, when blown with air from human lungs from an ordinary bubble making tool such as can be found at most toy stores within small bottles of bubble solution, tend to last for at least 1 minute before popping, often from 10 to 100 minutes before popping, and often more than 1,000 minutes before popping.

For the purposes of this document, 'invert sugar' is considered to be about a 50/50 blend of fructose and glucose, or any blend of fructose and glucose in the range of 25 to 50 percent of one component and 25 to 50 percent of the other component.

An example formulation for a liquid from which bubbles containing invert sugar can be made is as follows in Table 1. The numbers in the right column are parts by weight.

TABLE 1

| | |
|---|---|
| 523S Poly(vinyl) Alcohol | 4.5 |
| Original Regular Dawn Dish Detergent | 9.0 |
| Distilled Water | 40.5 |
| Karo Light Corn Syrup | 9.0 |
| Invert Sugar - KC Products | 9.0 |

A generalized formula for bubble solution containing is found in Table 2 below:

TABLE 2

| | |
|---|---|
| Water soluble polymer | 0 to 40 percent by weight |
| Invert sugar | 2 to 25 percent by weight |
| Water | 20 to 90 percent by weight |
| Surfactant | 0.5 to 25 percent by weight |
| Vegetable syrup | 0 to 40 percent by weight |

As desired, the invert sugar may be a blend of fructose and glucose that includes fructose in a range of from 25 to 75 weight percent and includes glucose in a range of 25 to 75 weight percent. If desired, the invert sugar may include a vegetable syrup such as a seed syrup.

While the formulations have been described and illustrated in conjunction with a number of specific examples, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations of lights described herein are to be considered in all respects as only illustrative, and not restrictive. All changes that come within the meaning and range of equivalency of the claims are to be embraced within their scope.

What is claimed is:

1. A solution for making long-lasting bubbles by a the force of air expelled from human lungs or by bubble-making toys or by bubble-making equipment, the solution comprising:
   not less than about 2 percent by weight of invert sugar,
   not less than about 20 percent by weight of water, and
   not less than about 0.5 percent by weight of a surfactant;
   wherein said percentages are calculated based on the total weight of said bubble solution.

2. A solution as recited in claim 1 further comprising:
   not less than about 5 percent by weight of vegetable syrup;
   wherein said percentage of vegetable syrup is calculated based on the total weight of said solution.

3. A solution as recited in claim 1 further comprising:
   not less than about 1 percent by weight of a water soluble polymer;
   wherein said percentage of water soluble polymer is calculated based on the total weight of said solution.

4. A solution as recited in claim 1 wherein said invert sugar is about a 50/50 mixture of glucose and fructose.

5. A solution as recited in claim 1 wherein said invert sugar is a blend of fructose and glucose that includes fructose in a range of from 25 to 75 weight percent and includes glucose in a range of 25 to 75 weight percent: wherein said weight percentages of fructose and glucose are calculated based on the total weight of said solution.

6. A solution as recited in claim 1 wherein bubbles made from said solution tend to last for at least 1 minute before popping.

7. A solution as recited in claim 2 wherein the vegetable syrup is a seed syrup.

8. A solution as recited in claim 3 wherein said water soluble polymer comprises alcohol.

9. A solution as recited in claim 7 wherein the seed syrup is corn syrup.

10. A solution as recited in claim 8 wherein the alcohol is polyvinyl alcohol.

11. A liquid solution for making long-lasting bubbles by a the force of air expelled from human lungs or by bubble-making toys or by bubble-making equipment, the bubble-making solution comprising:
   up to 40 percent by weight of a water-soluble polymer,
   up to 25% by weight of a surfactant,
   from about 20% to about 90% by weight of water, and
   from about 2% to about 25% by weight of invert sugar,
   the bubble-making solution being capable of forming bubbles when air is blown through it, and
   said invert sugar serving to cause said bubbles to remain intact and unpopped for a longer period of time than said bubble-making solution would if invert sugar were not present in it;
   wherein said weight percentages of fructose and glucose are calculated based on the total weight of said bubble-making solution.

12. A liquid solution for making long-lasting bubbles by a the force of air expelled from human lungs or by bubble-making toys or by bubble-making equipment, the bubble-making solution comprising:
   polyvinyl alcohol,
   a soap,
   water,
   vegetable syrup, and
   invert sugar;
   the bubble-making solution being capable of forming bubbles when air is blown through it, and
   said invert sugar serving to cause said bubbles to remain intact and unpopped for a longer period of time than said bubble-making solution would if invert sugar were not present in it.

13. A solution as recited in claim 12 wherein said invert sugar is about a 50/50 mixture of glucose and fructose.

14. A solution as recited in claim 12 wherein said invert sugar is a blend of fructose and glucose that includes fructose in a range of from 25 to 75 weight percent and includes glucose in a range of 25 to 75 weight percent; wherein said weight percentages of fructose and glucose are calculated based on the total weight of said solution.

* * * * *